United States Patent [19]
Shmulewitz

[11] Patent Number: 5,843,119
[45] Date of Patent: Dec. 1, 1998

[54] APPARATUS AND METHOD FOR DILATATION OF A BODY LUMEN AND DELIVERY OF A PROTHESIS THEREIN

[75] Inventor: Ascher Shmulewitz, Mercer Island, Wash.

[73] Assignee: United States Surgical Corporation, Norwalk, Conn.

[21] Appl. No.: 735,499

[22] Filed: Oct. 23, 1996

[51] Int. Cl.⁶ ................................................. A61M 29/00
[52] U.S. Cl. ............................................. 606/198; 604/96
[58] Field of Search .................. 604/96–104; 606/1, 606/108, 191–200; 623/1, 11, 12

[56] References Cited

U.S. PATENT DOCUMENTS

| | | |
|---|---|---|
| 3,868,956 | 3/1975 | Alfidi et al. . |
| 4,140,126 | 2/1979 | Choudhury . |
| 4,503,569 | 3/1985 | Dotter . |
| 4,562,596 | 1/1986 | Kornberg ..................................... 623/1 |
| 4,768,507 | 9/1988 | Fischell et al. . |
| 4,787,899 | 11/1988 | Lazarus ....................................... 623/1 |
| 4,878,906 | 11/1989 | Lindemann et al. . |
| 4,969,890 | 11/1990 | Sugita et al. ............................. 606/192 |
| 5,037,427 | 8/1991 | Harada et al. . |
| 5,078,726 | 1/1992 | Kreamer ................................... 606/194 |
| 5,089,005 | 2/1992 | Harada ..................................... 606/194 |
| 5,122,154 | 6/1992 | Rhodes . |
| 5,147,370 | 9/1992 | McNamara et al. .................... 606/108 |
| 5,147,385 | 9/1992 | Beck et al. . |
| 5,156,620 | 10/1992 | Pigott . |
| 5,197,978 | 3/1993 | Hess ............................................. 623/1 |
| 5,201,901 | 4/1993 | Harada et al. ............................ 606/198 |
| 5,211,658 | 5/1993 | Clouse ......................................... 623/1 |
| 5,219,355 | 6/1993 | Parodi et al. . |
| 5,316,023 | 5/1994 | Palmaz et al. . |
| 5,330,528 | 7/1994 | Lazim . |
| 5,360,443 | 11/1994 | Barone et al. .............................. 623/1 |
| 5,366,473 | 11/1994 | Winston et al. .......................... 606/198 |
| 5,387,235 | 2/1995 | Chuter ........................................ 623/1 |
| 5,443,495 | 8/1995 | Buscemi et al. ............................ 623/1 |
| 5,456,712 | 10/1995 | Maginot . |
| 5,456,713 | 10/1995 | Chuter ........................................ 623/1 |
| 5,464,449 | 11/1995 | Ryan et al. . |
| 5,466,242 | 11/1995 | Mori . |
| 5,476,505 | 12/1995 | Limon ........................................ 623/1 |
| 5,476,506 | 12/1995 | Lunn . |
| 5,489,295 | 2/1996 | Piplani et al. ............................... 623/1 |
| 5,503,636 | 4/1996 | Schmitt et al. . |
| 5,507,769 | 4/1996 | Marin et al. ............................. 606/198 |
| 5,522,882 | 6/1996 | Gaterud et al. ............................. 623/1 |
| 5,522,883 | 6/1996 | Slater et al. ................................ 623/1 |
| 5,534,024 | 7/1996 | Rogers et al. . |
| 5,536,252 | 7/1996 | Imran et al. ............................. 604/101 |
| 5,549,635 | 8/1996 | Solar . |
| 5,549,663 | 8/1996 | Cottone, Jr. . |
| 5,556,414 | 9/1996 | Turi . |
| 5,562,727 | 10/1996 | Turk et al. . |
| 5,562,728 | 10/1996 | Lazarus et al. . |
| 5,571,167 | 11/1996 | Maginot . |
| 5,571,170 | 11/1996 | Palmaz et al. . |
| 5,571,171 | 11/1996 | Barone et al. . |
| 5,571,172 | 11/1996 | Chin . |
| 5,578,071 | 11/1996 | Parodi . |
| 5,578,072 | 11/1996 | Barone et al. . |
| 5,591,228 | 1/1997 | Edoga . |
| 5,591,229 | 1/1997 | Parodi . |
| 5,632,760 | 5/1997 | Sheiban et al. ......................... 604/101 |

*Primary Examiner*—Glenn K. Dawson

[57] ABSTRACT

Apparatus and methods are provided for first expanding a body lumen of a body vessel or organ and then deploying a prosthesis to maintain the lumen patent. The apparatus includes a catheter having a balloon member formed of a biocompatible material, a balloon cutting element, and a thermally activated shape memory alloy prosthesis disposed within the balloon. The prosthesis is formed of nickel-titanium alloy having a reduced diameter in the martensite phase, and an expanded diameter in the austenite phase. The balloon member is inflated using a first fluid having a temperature below the martensite transition temperature to expand the body lumen and a second fluid having a temperature sufficient to cause the prosthesis to transition to the expanded diameter, trapping the material of the balloon member against the body wall. A cutting device disposed on the catheter then severs balloon member to release the prosthesis.

36 Claims, 3 Drawing Sheets

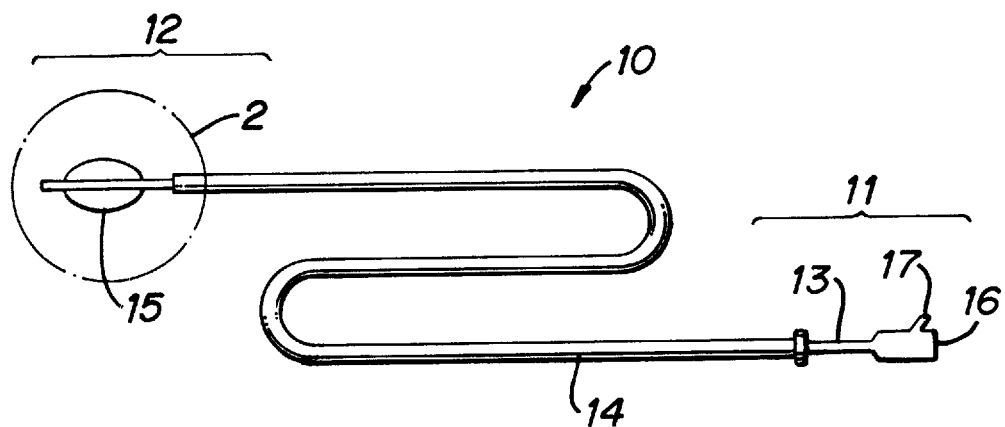
FIG_1
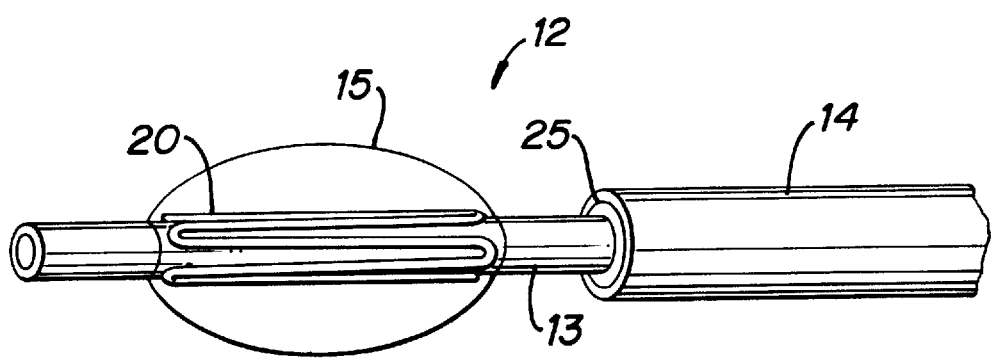
FIG_2
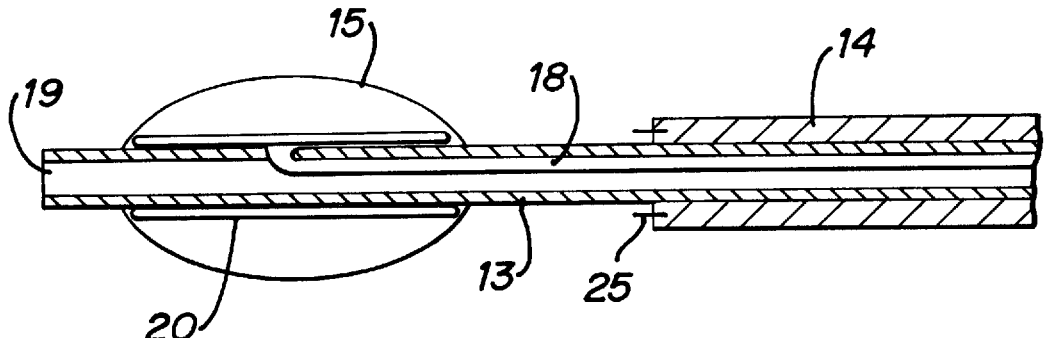
FIG_3

APPARATUS AND METHOD FOR DILATATION OF A BODY LUMEN AND DELIVERY OF A PROTHESIS THEREIN

FIELD Of THE INVENTION

The present invention relates to methods and apparatus for performing balloon dilatation of a body lumen, and for delivering a prosthesis therein, using a combined dilatation and prosthesis delivery system, and more particularly, for delivering a thermally activated shape memory alloy prosthesis.

BACKGROUND OF THE INVENTION

In recent years a number of prostheses have been developed for deployment in body lumens to maintain the patency of a vessel or organ following a mechanical dilatation procedure. Typically, a guide wire is routed to the area to be treated. A dilatation device, usually a balloon catheter, is then inserted transluminally along the guide wire to the site of the passage and inflated to expand the vessel. The balloon catheter is then withdrawn and a delivery system carrying an expandable prosthesis is delivered to the site of the former blockage by inserting it transluminally along the guide wire. The delivery system is then actuated to deploy the prosthesis, thereby retaining the lumen patent. The insertion of both catheters to the site of the blockage or narrowing is monitored using fluoroscopy or dye techniques.

For example, percutaneous transluminal angioplasty (PTA) is commonly used today as an alternative treatment to traditional coronary artery bypass grafting. Typically, such procedures involve the insertion of the balloon catheter within a coronary artery, and dilation of the balloon to crack plaque lining the artery, thus increasing the diameter of the artery and restoring flow therethrough. It is common practice to then deploy a vascular prosthesis, such as the Palmaz Stent® sold by Johnson & Johnson Interventional Systems, Inc., to maintain the expanded diameter of the vessel. That stent comprises a slotted metallic tubular member that is plastically deformed using a balloon catheter to maintain the patency of the vessel, and is described in U.S. Pat. No. 4,739,762.

Similar methods and apparatus are known for dilating other body organs, such as the urethra, in response to blockages or narrowing caused, for example, by hypertrophy of the prostate gland. Rosenbluth U.S. Pat. No. 4,672,128 describes a balloon deployable prosthesis which is expanded to both dilate the urethra and to simultaneously implant the prosthesis.

A drawback of many of the previously known dilatation and prosthesis delivery systems is that they require either the use of two separate catheters, as in the Palmaz system, or cannot adequately expand the body lumen during a simultaneous dilatation and prosthesis delivery step. In the two-catheter systems, a first catheter is required for dilating the vessel, and a second catheter is required for delivering the prosthesis. Moreover, the clinician must take care when inserting the prosthesis delivery system to ensure that the prosthesis is properly aligned with the portion of the body lumen dilated during the dilatation step of the procedure. Otherwise, the prosthesis may be delivered to an incorrect location within the body lumen, and the unsupported portion of the vessel may quickly restenose. With single catheter, single step systems, such as described in the Rosenbluth patent, it is not possible to fully dilate the vessel prior to, and separately from, the step of delivering the prosthesis.

It accordingly would be desirable to provide a single catheter arrangement for both fully dilating the body lumen and for delivering the prosthesis to the affected area, so as to reduce the cost and complexity of previously known procedures.

It also would be desirable to provide a combined dilatation and delivery system that would enable a clinician to reduce the time required to perform the procedure, by eliminating the need to insert and withdraw multiple catheters along the guide wire.

It further would be desirable to provide a combined dilatation and prosthesis delivery system that would enable the clinician to separately deploy the prosthesis after the dilatation procedure without requiring intermediate movement of the catheter, thereby ensuring that the prosthesis is delivered to the correct location within the body lumen.

SUMMARY OF THE INVENTION

In view of the foregoing, it is an object of this invention to provide apparatus and methods that enable steps of both fully dilating a body lumen and delivering a prosthesis to the dilated portion of the body lumen using a single catheter arrangement, thereby reducing the cost and complexity associated with previously known procedures.

It is another object of this invention to provide a combined dilatation and delivery system that enables a clinician to reduce the time required to perform the procedure, by eliminating the need to insert and withdraw multiple catheters along a guide wire.

It is a further object of this invention to provide a combined dilatation and prosthesis delivery system that enables separate deployment of the prosthesis, after the dilatation procedure, and without requiring intermediate movement of the catheter, thereby ensuring that the prosthesis is delivered to the correct location within the body lumen.

In accordance with principles of the present invention, apparatus comprising a dilatation system and prosthesis deployment system is provided for first expanding a body lumen of a body vessel or organ and then deploying a prosthesis to maintain the lumen patent.

Apparatus constructed in accordance with the principles of the present invention comprises a catheter having a balloon member formed of a biocompatible material, a balloon cutting element, and a thermally activated shape memory alloy prosthesis disposed within the balloon. In a preferred embodiment, the prosthesis is formed of a nickel-titanium alloy having a martensite phase transition temperature below body temperature, about 37° C. The prosthesis has a reduced diameter when in the martensite phase, and assumes an expanded diameter when it transitions to the austenite phase.

In accordance with methods of the present invention, the inventive apparatus is inserted transluminally in a body lumen along a guide wire until it reaches the site of the blockage or narrowing. When inserted, the prosthesis is in its reduced diameter state. The balloon member is then inflated using a first fluid having a temperature below the martensite transition temperature. The injected fluid expands the balloon member against the body lumen, thereby causing the body lumen to expand. The first fluid is then suctioned from the balloon member, causing it to deflate.

While the catheter is retained in position, a second fluid having a temperature sufficient to cause the prosthesis to transition into the austenite phase is then injected into the balloon, causing the mid-section of the prosthesis to expand outwardly against the body lumen, trapping the material of the balloon member against the body wall. A cutting device disposed on the catheter adjacent to the balloon member is then advanced, severing the material of the balloon member from the catheter and releasing the prosthesis.

Further features of the invention, its nature and various advantages will be more apparent from the accompanying drawings and the following detailed description of the preferred embodiments.

BRIEF DESCRIPTION OF THE DRAWINGS

FIG. 1 is a perspective view of a combined dilatation and prosthesis delivery system constructed in accordance with the present invention;

FIG. 2 is a perspective view of the distal end region of the apparatus of FIG. 1;

FIG. 3 is a sectional view of the apparatus of FIG. 1;

DETAILED DESCRIPTION OF THE INVENTION

Figure 4:
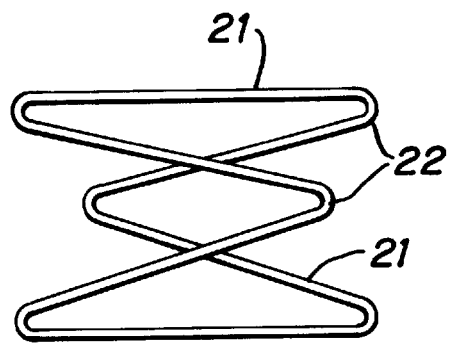
FIG. 4 is an illustrative embodiment of a prosthesis suitable for use with the apparatus of the present invention.

As described hereinbelow the apparatus and methods of the present invention enable a clinician to both fully dilate and deploy a prosthesis in a body lumen using a single catheter arrangement, and without intermediate movement of the catheter. In addition, the apparatus of the present invention enables a clinician to adjust the position of a prosthesis even after it has been partially deployed.

Referring to FIGS. 1–3, apparatus 10 constructed in accordance with the principles of the present invention is described. Apparatus 10 includes proximal region 11 and distal end region 12, and comprises inner dual lumen catheter 13 covered by outer sheath 14. Distal end region 12, shown in greater detail in FIGS. 2 and 3, includes balloon member 15 containing prosthesis 20, while proximal region 11 includes guide wire port 16 and port 17 for inflating and deflating balloon member 15 via inflation lumen 18. Central lumen 19 permits apparatus 10 to be inserted transluminally along a conventional guide wire.

Inner dual lumen catheter 13 is formed of materials well known in the art, such as polyethylene or polyurethane. Balloon member 15 comprises a biocompatible material, such as nylon, polyethylene teraphthalate, or polyurethane, and is bonded to inner dual lumen catheter 13 using conventional techniques such as gluing, thermowelding, etc. Balloon member 15 is coupled to port 17 via inflation lumen 18 of inner dual lumen catheter 13.

Outer sheath 14 is disposed on inner catheter 13 for sliding movement in the proximal and distal directions. Outer sheath 14 includes cutting element 25 disposed on the end face nearest balloon member 15, for the purpose described herein below. Outer sheath 14 comprises a material commonly used in catheters, such as polyethylene, while cutting element 25 may comprise a sharpened band of stainless steel set in the distal end face of the outer sheath.

In accordance with the present invention, prosthesis 20 is sealed within balloon member 15 during manufacture of apparatus 10. Prosthesis 20, illustratively shown in FIG. 4, preferably comprises a series of substantially straight segments 21 interconnected by U-shaped turns 22, and is preferably formed of an alloy of about equal atomic weights of nickel and titanium, often referred to as "nitinol." Devices made of such nickel-titanium alloys are well known for possessing thermal shape memory characteristics.

Prosthesis 20 of the present invention exploits a feature of nitinol alloys known as one-way shape memory. This feature enables a nitinol device to be trained to have a desired expanded diameter when in the high temperature (austenite) phase. When cooled to a low temperature (martensite) phase, the device may be deformed to a reduced diameter. Upon application of heat sufficient to again raise the device into the austenite phase, the device expands to the desired expanded diameter while undergoing the phase transition. Prosthesis 20 of the present invention is selected to have an expanded diameter the same or slightly larger than the body lumen into which the prosthesis is to be deployed, and a martensite phase transition temperature of about 37° C.

During manufacture of apparatus 10, the prosthesis first is trained using techniques, per se known, to have a desired expanded diameter, cooled into the martensite phase, and then deformed to a reduced diameter. As is typical for nitinol devices, prosthesis 20 remains at the reduced diameter at room temperature. Prosthesis 20 is then placed within balloon member 15 and balloon member is affixed to inner dual lumen catheter 13. Prosthesis 20 remains in the reduced diameter when at room temperature once encapsulated within balloon member 15.

Figure 5A:
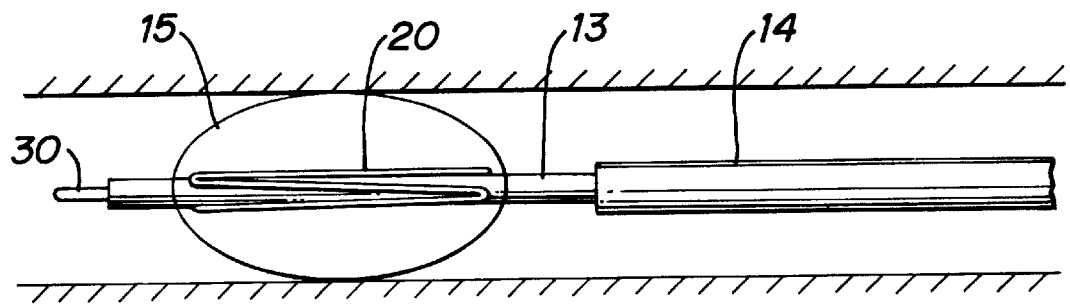
FIGS. 5A–5D depict the steps of the method in accordance with the present invention of first dilating a body lumen and then deploying a prosthesis using the apparatus of FIGS. 1–3.

Referring now to FIGS. 5A to 5D, a method of using the apparatus of FIG. 1 to fully dilate a body lumen and deploy a prosthesis therein are described. In FIG. 5A, apparatus 10 is shown inflated within a body lumen, for example, an artery, after having been inserted transluminally into the body lumen along guide wire 30. As is conventional, guide wire 30 is first inserted into the lumen. The proximal end of guide wire 30 is then fed into apparatus 10 via lumen 19 of inner dual lumen catheter 13, and the apparatus is advanced along guide wire 30 until it is disposed at a desired position within the body lumen (for example, as determined by fluoroscopy or dye injection).

Once positioned within the body lumen, port 17 in proximal region 11 of catheter 13 is coupled to a source of cooled fluid, such as a syringe of cooled saline solution, and the cooled fluid is injected into balloon member 15. When the cooled fluid is injected into balloon member 15, the balloon member expands into contact with the body lumen, thereby expanding the body lumen to a larger diameter. The injected fluid serves not only to pressurize the balloon member to effect dilatation of the body lumen, but also keeps prosthesis 20 from prematurely expanding due to body heat.

When the body lumen is adequately expanded, as may be determined, for example, by employing a contrast agent in the cooled fluid injected into the balloon member, the cooled fluid is withdrawn. A heated fluid is then injected via port 17 into balloon member 15 via lumen 18. The heated fluid, which preferably has a temperature greater than the transition temperature of prosthesis 20, causes the prosthesis to transition to its expanded diameter.

Figure 5B:
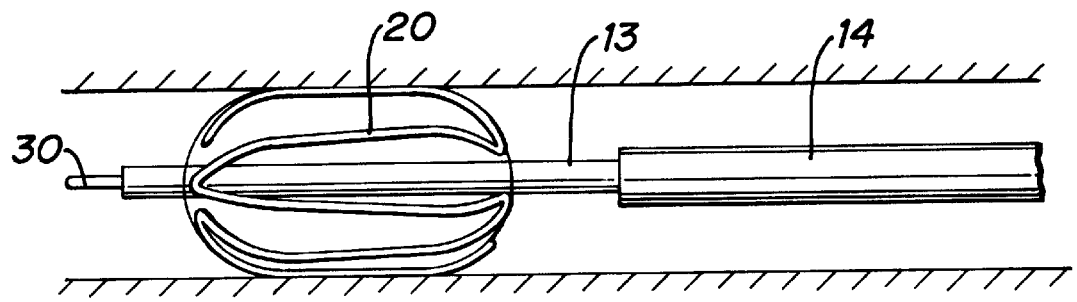

As depicted in FIG. 5B, while the mid-section of prosthesis 20 expands into contact with the body lumen, the U-shaped turns at the ends of the prosthesis preferably remain constrained by the ends of the balloon member (where the balloon member is bonded to inner catheter 13). If the heated fluid also contains a contrast agent, the clinician may then adjust the position of apparatus 10 within the body lumen under fluoroscopic guidance.

Figure 5C:
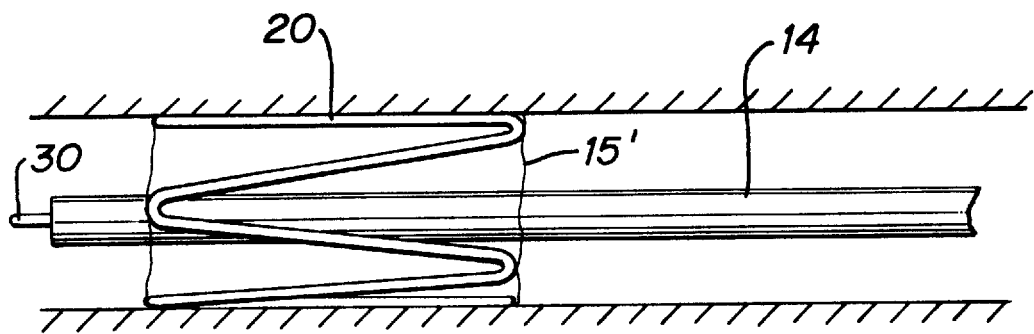

The clinician then advances outer sheath 14 so that cutting element 25 severs the balloon material near the bond site, just slightly inward of the constrained edges of prosthesis 20. Advancement of outer sheath 14 may be by linear displacement, although rotation of outer sheath 14 and cutting element may facilitate severing of the balloon member. As illustrated in FIG. 5C, when the cutting element 25 severs balloon member 15, the constraint on the U-shaped ends of the prosthesis force the balloon material flush against the wall of the body lumen. In this manner, the ends of balloon material 15' are prevented from extending into the body lumen, and therefore do not serve as sites of thrombus formation.

Figure 5D:
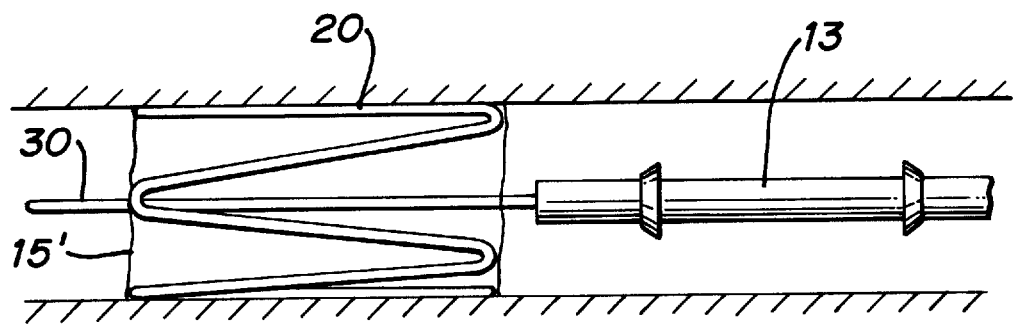

Once the proximal and distal ends of the balloon member are severed from catheter 13 by cutting element 25 of outer sheath 14, the balloon material and prosthesis are free from the apparatus 10, with the balloon member material 15' trapped between the wall of the body lumen and prosthesis 20. FIG. 5D depicts apparatus 10 of the present invention after deployment of prosthesis 20. Outer sheath 14 is shown in a retracted position, revealing the remnants of the balloon member 15 at the bond sites after operation of the cutting element.

As will be apparent to one of skill in the art, balloon material 15', once severed from apparatus 10, may function as a fluid impermeable graft. In this case, prosthesis 20 and balloon material 15' constitute, respectively, the stent and graft of a stent-graft combination. Accordingly, apparatus 10 may be used not only in conventional situations for maintaining a body lumen patent, but also finds use in applications, for example, where it is desired to isolate an aneurysm or fistula.

In alternative embodiments of the present invention, prosthesis 20 may be formed of a nitinol alloy exhibiting two-way shape memory characteristics, i.e., assuming a first predetermined shape in the martensite phase and a second predetermined shape in the austenite phase. Where prosthesis 20 is formed of a two-way shape memory alloy, the clinician may not only adjust the position of the prosthesis after it is partially deployed (i.e., heated to expand, but before the balloon member is severed), but the clinician may even choose to inject a cooled fluid to contract the prosthesis, should he or she desire to abort the procedure.

In another alternative embodiment of the apparatus of the present invention, balloon member 15 and prosthesis 20 may be arranged so that upon expansion of the prosthesis, the ends of the prosthesis automatically perforate the balloon member as the prosthesis expands, thereby fully deploying the prosthesis in the body lumen without the need for a separate step of severing the balloon. In addition, other configurations of prosthesis 20 may be employed, for example, prosthesis 20 may comprise a coiled planar shape or sheet made of a shape memory alloy.

While preferred illustrative embodiments of the invention are described above, it will be obvious to one skilled in the art that various changes and modifications may be made therein without departing from the invention and the appended claims are intended to cover all such changes and modifications which fall within the true spirit and scope of the invention.

What is claimed is:

1. Apparatus for dilating a body lumen and retaining the body lumen patent, the apparatus comprising:

a catheter having a proximal end region and a distal end region;

a balloon member disposed adjacent the distal end region for expanding an inner dimension of the body lumen, the balloon member comprising a biocompatible material;

a prosthesis at least partially disposed within the balloon member, the prosthesis having a first shape of reduced dimension and a second shape of expanded dimension; and means for severing the balloon member from the distal end region of the catheter.

2. The apparatus as defined in claim 1 wherein the means for severing the balloon comprises:

an outer sheath disposed on the catheter, the outer sheath having a distal end; and a cutting element disposed on the distal end of the outer sheath.

3. The apparatus as defined in claim 2 wherein the outer sheath is longitudinally advanceable such that the cutting element cuts the balloon member.

4. The apparatus as defined in claim 3 wherein the outer sheath is adapted to rotate during longitudinal advancement thereof.

5. The apparatus as defined in claim 1 wherein the prosthesis comprises a shape memory alloy.

6. The apparatus as defined in claim 5 wherein the prosthesis has a martensite transition temperature about equal to body temperature.

7. The apparatus as defined in claim 5 wherein the prosthesis exhibits one-way thermally activated shape memory.

8. The apparatus as defined in claim 5 wherein the prosthesis exhibits two-way thermally activated shape memory.

9. The apparatus as defined in claim 1 wherein the prosthesis includes ends that are constrained by the balloon member when the prosthesis is in the second shape, so that the biocompatible material is forced against the body lumen when the prosthesis is in the second shape.

10. The apparatus as defined in claim 1 wherein the prosthesis comprises a plurality of pairs of substantially straight segments, each of the pairs connected by a U-shaped turn.

11. The apparatus as defined in claim 1 wherein the balloon member, once severed from the catheter, forms a fluid impermeable graft.

12. An apparatus for dilating a body lumen, the apparatus comprising;

a catheter having a proximal end region and a distal end region;

a balloon member comprising a biocompatible material disposed on the distal end region;

a stent confined within the balloon member, the stent having a first shape of reduced dimension and a second shape of expanded dimension; and means for severing the balloon member from the distal end region of the catheter when the stent is in the second shape such that at least a portion of the balloon member is captured between the stent and an inner wall of the body lumen.

13. The apparatus as defined in claim 12 wherein the means for severing the balloon comprises:

an outer sheath disposed on the catheter, the outer sheath having a distal end; and a cutting element disposed on the distal end of the outer sheath.

14. The apparatus as defined in claim 12 wherein the stent comprises a shape memory alloy.

15. The apparatus as defined in claim 14 wherein the stent has a martensite transition temperature about equal to body temperature.

16. The apparatus as defined in claim 12 wherein the stent includes ends that are constrained by the balloon member when the stent is in the second shape, so that the biocompatible material is forced against the body lumen when the stent is in the second shape.

17. A method of dilating a body lumen and disposing a prosthesis within the body lumen, the method comprising steps of:

provding an apparatus having a proximal end region and a distal end region, a balloon member formed of a biocompatible material disposed on the distal end region, a prosthesis at least partially disposed within the balloon member, the prosthesis having a first shape of reduced dimension and a second shape of expanded dimension;

inserting the distal end region of the apparatus to a desired position within the body lumen;

inflating the balloon member to expand the body lumen;

expanding the prosthesis to the second shape within the balloon member; and severing the balloon member from the apparatus to deploy the prosthesis.

18. The method as defined in claim 17 wherein the apparatus includes means for severing the balloon member, and wherein the step of severing includes the step of actuating the severing means.

19. The method as defined in claim 17 wherein the step of providing further comprises providing an apparatus having a prosthesis formed of a thermally activated shape memory alloy.

20. The method as defined in claim 19 wherein the step of inflating comprises the step of introducing a fluid having a temperature below the transition temperature of the prosthesis into the balloon member to expand the balloon member.

21. The method as defined in claim 20 wherein the step of expanding comprises the step of introducing a fluid having at temperature above the transition temperature of the prosthesis into the balloon member.

22. Apparatus for maintaining patency of a body vessel, which comprises:

an elongated member defining a longitudinal axis and having proximal and distal ends, and being adapted to be positioned within a body vessel;

an expandable member mounted to the elongated member and expandable to engage inner wall portions of the body vessel; and a prosthesis at least partially disposed within the expandable member, the prosthesis moveable to a deployed position to retain the expandable member against the inner wall portion of the body vessel and maintain an inner dimension of a lumen of the body vessel.

23. The apparatus according to claim 22 further including a cutting member mounted to the elongated member to cut the expandable member to release at least a portion of the expandable member from the elongated member.

24. The apparatus according to claim 23 wherein the expandable member is an inflatable balloon membrane.

25. The apparatus according to claim 24 wherein the elongated member includes an inflation passageway to permit passage of inflation fluids to the balloon membrane to inflate the balloon membrane.

26. The apparatus according to claim 25 wherein the prosthesis is enclosed within the balloon membrane.

27. The apparatus according to claim 26 wherein the cutting member is longitudinally moveable to cut the balloon membrane to release at least a portion of the balloon membrane and the prosthesis from the elongated member.

28. The apparatus according to claim 27 wherein the prosthesis comprises a thermally activated shape memory material.

29. An apparatus for maintaining the patency of a body vessel, which comprises:

a catheter defining a longitudinal axis and having proximal and distal end portions, and having an inflation channel associated therewith for passage of inflation media;

a balloon member mounted adjacent the distal end portion of the catheter and in communication with the inflation channel, the balloon member inflatable to engage an inner wall of the body vessel;

a stent disposed within the balloon member, the stent comprising a shape memory material and being capable of moving from an initial condition to an expanded condition in response to a predetermined temperature level of inflation media introduced within the balloon member, to retain the balloon member against the inner wall of the body vessel and maintain the patency of the body vessel; and a cutting member mounted with respect to the catheter and longitudinally movable to sever the balloon member from the catheter, to thereby release the balloon member and the stent within the body vessel.

30. A method for maintaining the patency of a body organ, comprising the steps of:

positioning an elongated member into a body passage, the elongated member including an inflatable membrane and a prosthesis at least partially disposed within the inflatable membrane;

inflating the inflatable membrane to cause engagement thereof with the inner wall portion of the body organ; and expanding the prosthesis to cause engagement thereof with the inflatable membrane to maintain the inflatable membrane against the inner wall portion to thereby maintain the patency of the body organ.

31. The method according to claim 30 including the step of releasing the inflatable membrane and the prosthesis from the elongated member.

32. The method according to claim 31 including the step of removing the elongated member from the body passage thereby leaving the inflatable membrane and the prosthesis within the body organ.

33. The method according to claim 32 wherein the elongated member includes a cutting member associated therewith and wherein the step of releasing includes actuating the cutting membrane to sever at least a portion of the inflatable member from the elongated member.

34. The method according to claim 33 wherein the prosthesis comprises a thermally activated shape memory material and wherein the step of expanding includes subjecting the prosthesis to a temperature to cause the prosthesis to expand.

35. The method according to claim 34 wherein the elongated member includes an inflation channel in communication with the inflatable membrane and wherein the step of expanding includes introducing fluid through the inflation channel and into the inflatable membrane, the inflation fluid being at a temperature to cause the prosthesis to expand.

36. The method according to claim 35 wherein the inflatable membrane comprises a biocompatible material and wherein the step of expanding includes arranging the inflatable membrane to serve as a graft for the body organ.

* * * * *